(12) United States Patent
Moir et al.

(10) Patent No.: US 7,955,812 B2
(45) Date of Patent: Jun. 7, 2011

(54) METHODS OF DIAGNOSING ALZHEIMER'S DISEASE BY DETECTING ANTIBODIES TO CROSS-LINKED β-AMYLOID OLIGOMERS

(75) Inventors: Robert Moir, Scituate, MA (US);
Rudolph Tanzi, Hull, MA (US)

(73) Assignee: The General Hospital Corporation, Boston, MA (US)

( * ) Notice: Subject to any disclaimer, the term of this patent is extended or adjusted under 35 U.S.C. 154(b) by 518 days.

(21) Appl. No.: 11/632,784

(22) PCT Filed: Jul. 19, 2005

(86) PCT No.: PCT/US2005/025567
§ 371 (c)(1),
(2), (4) Date: Jul. 15, 2008

(87) PCT Pub. No.: WO2006/014638
PCT Pub. Date: Feb. 9, 2006

(65) Prior Publication Data
US 2008/0267952 A1    Oct. 30, 2008

Related U.S. Application Data

(60) Provisional application No. 60/589,081, filed on Jul. 19, 2004.

(51) Int. Cl.
*G01N 33/53* (2006.01)
*G01N 33/543* (2006.01)
*G01N 33/566* (2006.01)
*G01N 33/96* (2006.01)

(52) U.S. Cl. .................................................. 435/7.94
(58) Field of Classification Search .................. None
See application file for complete search history.

(56) References Cited

FOREIGN PATENT DOCUMENTS

| WO | WO 99/27944 A1 | 6/1999 |
|---|---|---|
| WO | WO 02/00245 A1 | 1/2002 |
| WO | WO 03/104437 A2 | 12/2003 |

OTHER PUBLICATIONS

Weksler 2002 (Experimental Gerontology 37:943-948).*
Du 2001 (Neurology 57:801-805).*
Xu 1997 (Mechanisms of Ageing and Development 94:213-222).*
Head 2001 (Neurobiology of Disease 8:792-806).*
Atwood, C. S. et al., "Copper Mediates Dityrosine Cross-Linking of Alzheimer's Amyloid-β," *Biochemistry* 2004; 43:560-568.
Atwood, C. S. et al., "Copper Catalyzed Oxidation of Alzheimer Aβ," *Cellular and Molecular Biology* 2000; 46(4):777-783.
Bush, A. I. et al., "The galvanization of β-amyloid in Alzheimer's disease," *PNAS* May 28, 2002; 99(11):7317-7319.
Gong, Y. et al., "Alzheimer's disease-affected brain: Presence of oligomeric Aβ ligands (ADDLs) suggests a molecular basis for reversible memory loss," *PNAS* Sep. 2, 2003; 100(18):10417-10422.
Hock, C. et al., "Antibodies against β-Amyloid Slow Cognitive Decline in Alzheimer's Disease," *Neuron* May 22, 2003; 38:547-554.
Moir, R. D. et al., "Autoantibodies to Redox-modified Oligomeric Aβ Are Attenuated in the Plasma of Alzheimer's Disease Patients," *The Journal of Biological Chemistry* Apr. 29, 2005; 280(17):17458-17463.
Roher, A. E. et al., "Morphology and Toxicity of Aβ-(1-42) Dimer Derived from Neuritic and Vascular Amyloid Deposits of Alzheimer's Disease," *The Journal of Biological Chemistry* Aug. 23, 1996; 271(34):20631-20635.
Walsh, D. M. et al., "The Oligomerization of Amyloid β-Protein Begins Intracellularly in Cells Derived from Human Brain," *Biochemistry* 2000; 39:10831-10839.

* cited by examiner

*Primary Examiner* — Daniel E Kolker
(74) *Attorney, Agent, or Firm* — Wolf, Greenfield & Sacks, P.C.

(57) ABSTRACT

The invention relates to antibodies that bind cross-linked amyloid β oligomers, and methods for using such antibodies for diagnosis and treatment of Alzheimer's disease.

7 Claims, 3 Drawing Sheets

METHODS OF DIAGNOSING ALZHEIMER'S DISEASE BY DETECTING ANTIBODIES TO CROSS-LINKED β-AMYLOID OLIGOMERS

RELATED APPLICATIONS

This application is a national stage filing under 35 U.S.C. §371 of international application PCT/US2005/025567, filed Jul. 19, 2005, which was published under PCT Article 21(2) in English, and claims priority under 35 U.S.C. 119(e) to U.S. Provisional Patent Application Ser. No. 60/589,081, which was filed on Jul. 19, 2004, and is incorporated herein by reference.

FIELD OF THE INVENTION

The invention relates to antibodies that bind cross-linked amyloid β oligomers, and methods for using such antibodies. The invention is useful for diagnosing, and treating Alzheimer's disease.

BACKGROUND OF THE INVENTION

A convergence of histological, biochemical and genetic evidence links the widespread neuronal loss characteristic of Alzheimer's disease (AD) with deposits of β-amyloid that pervade the brains of AD patients. The principal component of extracellular β-amyloid is the β-amyloid protein (Aβ). The Aβ peptide is not directly expressed as a functional protein entity[1] but is released by the processing of the much larger amyloid protein precursor (APP) protein[2, 3]. Aβ appears to be a normal product of cellular APP catabolism and is found as a soluble component of human cerebrospinal fluid (CSF) and plasma[4-6]. While Aβ can contain between 39 and 43 amino acids, the predominant species in brain are Aβ40 (40 residues) and Aβ42 (42 residues)[7, 8]. Analysis of material purified from human tissue suggest that up to 40% of the Aβ pool in AD brain consists of low molecular weight cross-linked β-amyloid protein species we have coined "CLAPS"[9]. Covalent cross-linking of Aβ appears to involve oxidation of the protein, which is tied to the peptide's propensity to bind the redox active metals copper and iron[10]. The mechanism of Aβ neurotoxicity remains controversial. However, evidence is mounting that the most neurotoxic forms of Aβ are not mature fibrils but prefibrillar oligomers or protofibrils[11], which would include CLAPS. Notably, recent studies have demonstrated that the most toxic CLAPS maybe cross-linked dimeric species of Aβ[12, 13]. Despite the abundance and harmful bioactivity shown for CLAPS, the vast majority of currently available data has focused on non-oxidized monomeric forms of the peptide.

Interest in autoimmunity to Aβ has been stimulated by recent findings that amyloid burden in transgenic animal models can be attenuated by circulating anti-Aβ antibodies[14-16]. β-amyloid deposition can be inhibited by either peripheral infusion of exogenous anti-Aβ antibodies (passive immunization) or autoimmunity induced by immunization with synthetic Aβ peptide. Initial studies suggested anti-Aβ antibodies aid in the clearance of amyloid by crossing the blood brain barrier (BBB) and binding directly to plaques. However, subsequent studies have suggested that antibodies[17] and other Aβ binding agents[18] may not need to cross the BBB to be effective in inhibiting cerebral Aβ plaque formation. In this model, Aβ is bound and sequestered in the periphery and prevented from crossing back into the brain, thus promoting a net flux out of neurological tissue[17].

Whatever the mechanism, the use of circulating anti-Aβ antibodies is a therapeutic strategy being actively pursued. Unfortunately, dosing in the first clinical trial using Aβ vaccination to treat AD patients was terminated in phase II because of complications associated with inflammation of the CNS vasculature[19]. None the less, limited data suggest that amyloid load may have been attenuated in some trial subjects by autoantibodies specific for insoluble Aβ deposited as Aβ-amyloid[20]. Despite the earlier problems, clinical trials aimed at elevating anti-Aβ antibody levels in AD patients will most likely proceed. Therefore, it is imperative to advance our understanding of the autoimmune response to Aβ and its derivatives with greater alacrity.

The presence of anti-Aβ immunoreactivity in human serum and CSF was first reported in 1991 by Mönning et al.[21]. Subsequently, Epstein-Barr virus (EBV) transformed B cells from AD patients have been shown to secrete anti-AD antibodies[22]. More recently, several studies have used ELISA assays to compare anti-Aβ autoimmunoreactivity in control and AD plasma and CSF. However, a consensus has yet to emerge as to whether anti-Aβ autoantibodies are elevated[23], depressed[24, 25] or unchanged[26] in AD patients compared to non-demented controls. The future success of AD therapies based on anti-Aβ antibodies will require greater delineation of the naturally occurring autoantibodies to Aβ.

Although a pattern of decline in AD patients is generally clinically recognizable as the disease progresses, reliable diagnostic methods are lacking. The only definitive diagnostic test for AD at this time is to determine whether amyloid plaques and tangles are present in a subject's brain tissue, a determination that can only be done after death. Thus, due to the lack of suitable diagnostic methods, health-care professionals are only able to provide a tentative diagnosis of AD in an individual, particularly at the early to mid stages of the disease. Although these diagnoses can indicate that a person "likely" has AD, the absence of a definitive diagnosis reflects a critical need for more accurate and reliable AD diagnostic tests.

In addition to the absence of reliable diagnostic methods, the are also very limited treatment options available for patients suspected of having and/or diagnosed as having AD. Several drugs have been approved in the US for treatment of early and mid-stage AD, but they have significant detrimental side effects and limited efficacy. The lack of effective treatments for AD means that even with a diagnosis of probable AD, the therapeutic options are quite limited. Thus, there is a significant need for effective compounds and methods for preventing and/or treating AD.

SUMMARY OF THE INVENTION

Experiments to date have used synthetic unmodified monomeric Aβ peptides to test autoimmunity. The current study is the first to test human plasma for specific anti-CLAPS antibodies. We present data suggesting that CLAPS generated by exposing Aβ to mild redox conditions may be more immunogenic than the normal unmodified, monomeric Aβ species. We also show that plasma taken from AD patients exhibit significantly less immunoreactivity to CLAPS than do plasma samples drawn from non-demented controls. Moreover, lower anti-CLAPS antibody titers correlated with earlier age-at-onset (AAO) of AD. These findings are consistent with an association between AD pathology and autoantibodies specific to cross-linked Aβ species.

According to one aspect of the invention, methods for diagnosing Alzheimer's disease in a subject are provided. The methods include obtaining a biological sample from a subject, and determining the presence of antibodies reactive with oxidized forms of amyloid β in the blood or plasma sample. The lack of antibodies reactive with oxidized forms of amyloid β, or a reduced level of antibodies reactive with oxidized forms of amyloid β relative to a control, indicates that the subject has Alzheimer's disease. In preferred embodiments, the biological sample is a blood sample or plasma sample.

In some embodiments, the oxidized forms of amyloid β used to determine the presence of antibodies are cross-linked β-amyloid protein species (CLAPS), preferably the CLAPS are 15-35 kDa. In other embodiments, the CLAPS are formed by oxidation of amyloid β with horse radish peroxidase in the presence of hydrogen peroxide.

In certain embodiments, the method used to determine the presence of antibodies reactive with oxidized forms of amyloid β is an ELISA assay. Preferably the ELISA assay is a sandwich ELISA assay.

In other embodiments, the control is blood or plasma from a non-demented individual.

According to another aspect of the invention, methods for inducing an immune response to an oxidized form of amyloid β are provided. The methods include administering to a subject an amount of an oxidized form of amyloid β effective to induce a specific immune response to the oxidized form of amyloid β. Preferably the immune response is the production of antibodies that bind to the oxidized form of amyloid β.

In certain embodiments, the oxidized form of amyloid β is cross-linked β-amyloid protein species (CLAPS). Preferably the CLAPS are 15-35 kDa. In other embodiments, the CLAPS are formed by oxidation of amyloid β with horse radish peroxidase in the presence of hydrogen peroxide.

In a further aspect of the invention, methods for treating or preventing Alzheimer's disease are provided. The methods include administering to a subject in need of such treatment an amount of antibodies, or binding fragments thereof, that bind to an oxidized form of amyloid β.

In certain embodiments, the antibodies are made by administering an oxidized form of amyloid β to a mammal to produce antibodies that bind the oxidized form of amyloid β. Preferably the oxidized form of amyloid β is cross-linked β-amyloid protein species (CLAPS), particularly CLAPS of 15-35 kDa.

In some embodiments, the mammal is a nonhuman species comprising human immunoglobulin genes, preferably a mouse.

In preferred embodiments, the antibodies or fragments thereof are human antibodies, humanized antibodies or chimeric antibodies, or antigen-binding fragments thereof. Preferred antibody fragments include Fab fragments, F(ab')$_2$ fragments, and Fv fragments. In other embodiments the antibodies are single chain antibodies.

Use of oxidized forms of amyloid β, e.g., CLAPS, in the preparation of a medicament also is provided. Use of antibodies that specifically bind to oxidized forms of amyloid β, e.g., CLAPS, in the preparation of a medicament also is provided. The medicaments useful, in preferred embodiments, for increasing immune responses to oxidized forms of amyloid β, e.g., CLAPS, and for treating Alzheimer's disease and other disorders of amyloid β accumulation.

These and other objects of the invention will be described in further detail in connection with the detailed description of the invention.

BRIEF DESCRIPTION OF THE FIGURES

FIG. 1: Anti-Aβ ELISA is specific for anti-Aβ autoantibodies in human plasma.

DETAILED DESCRIPTION OF THE INVENTION

Figure 1A:
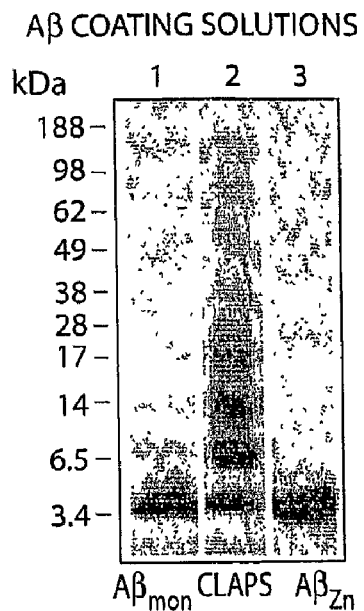
FIG. 1a: SDS extraction of Aβ coated wells. Microplate wells were incubated with Aβ that was unmodified, pre-treated with HRP, or in Zn(II)-histidine buffer. Wells were then extracted with SDS sample buffer. Extracts were immunoblotted, probed with pAb pan Aβ and developed for exposure to ECL-film. Wells coated with unmodified Aβ (Aβ$_{mon}$, lane 1) or peptide incubated in the presence of zinc (Aβ$_{Zn}$, lane 3) were monomeric. Material pre-treated with HRP (CLAPS, lane 2) contained SDS-stable oligomeric Aβ species consistent with redox modifications and covalent cross-linking.

We have discovered that human plasma contains antibodies that selectively bind CLAPS. The data presented below shows that plasma samples taken from Alzheimer's disease (AD) patients exhibit significantly less immunoreactivity to CLAPS than do plasma samples drawn from non-demented controls. Moreover, lower anti-CLAPS antibody titers correlated with earlier age-at-onset (AAO) of AD. These findings are consistent with an association between AD pathology and autoantibodies specific to cross-linked Aβ species. As used herein, CLAPS are one type of oxidized form of amyloid β, also referred to herein as "oxidized Aβ oligomers". This invention is not intended to be limited to CLAPS, but is applicable to other oxidized Aβ oligomers. Preferred oligomers are 15-35 kDa redox-modified Aβ oligomers.

Although the invention is primarily described in terms of Alzheimer's disease, other diseases or disorders in which the accumulation of amyloid β (Aβ) contributes to disease onset or progression also can be modulated and diagnosed in accordance with the invention. These disorders are generically known as Aβ-accumulation-associated disorders. As used herein, the term "Aβ-accumulation-associated disorder" means Alzheimer's disease, Down's syndrome, cerebrovascular amyloidosis, inclusion body myositis and hereditary inclusion body myopathies. Other Aβ-accumulation-associated disorders include any disease associated with abnormal (increased) BACE (β-site amyloid precursor protein cleaving enzyme) activity and any disease associated with abnormal (increased) γ-secretase activity.

The invention involves a variety of assays based upon detecting the level of antibodies in biological samples taken from subjects that bind oxidized forms of amyloid β, particularly cross-linked β-amyloid protein species (CLAPS). The assays include (1) characterizing the levels of the antibodies in a subject as a means of diagnosing Alzheimer's disease or other Aβ-accumulation-associated disorders; (2) evaluating a treatment for regulating levels of amyloid β, particularly of oxidized forms of amyloid β, in a subject; (3) selecting a treatment for regulating levels of amyloid β, particularly of oxidized forms of amyloid β, in a subject; and (4) determining regression, progression or onset of a condition characterized by abnormal levels of amyloid β, particularly of oxidized forms of amyloid β, in a subject.

Thus, subjects can be characterized, treatment regimens can be monitored, treatments can be selected and diseases can be better understood using the assays of the present invention. For example, the invention provides in one aspect a method for measuring the level of antibodies reactive with oxidized Aβ oligomers, such as CLAPS, in a subject. As provided by the invention, a low (or undetectable) level of antibodies reactive with oxidized Aβ oligomers is indicative of Alzheimer's disease in the subject. In particular, a level of antibodies reactive with oxidized Aβ oligomers such as CLAPS that is significantly lower in a subject than a control level (e.g., in a sample taken from a non-demented control individual) indicates that the subject has Alzheimer's disease, whereas a relatively normal level of antibodies indicates that the subject does not have Alzheimer's disease.

The assays described herein are carried out on samples obtained from subjects. As used herein, a subject is a human, non-human primate, cow, horse, pig, sheep, goat, dog, cat, or rodent. In all embodiments, human subjects are preferred.

Samples of tissue and/or cells for use in the various methods described herein can be obtained through standard methods. Samples can be surgical samples of any type of tissue or body fluid. Samples can be used directly or processed to facilitate analysis. Exemplary samples include a blood or serum sample, a cerebrospinal fluid sample, a bodily fluid, a cell, a cell scraping, a cell extract, a tissue biopsy, including punch biopsy, a tumor biopsy, a tissue, or a tissue extract or other methods. Preferably the samples are serum samples or blood samples.

Particular subjects to which the present invention can be applied are subjects at risk for, suspected of having, or known to have an Aβ-accumulation-associated disorder. Such disorders may include, but are not limited to: Alzheimer's disease and any other diseases associated with overproduction of Aβ or reduced clearance of Aβ such as Down's syndrome, cerebrovascular amyloidosis, inclusion body myositis and hereditary inclusion body myopathies.

Importantly, levels of antibodies that bind oxidized Aβ oligomers are preferably compared to controls according to the invention. The control may be a predetermined value, which can take a variety of forms. It can be a single value, such as a median or mean. It can be established based upon comparative groups, such as in groups having normal amounts of such antibodies and groups having abnormal (i.e., low) amounts of such antibodies. Another example of comparative groups would be groups having a particular disease (e.g., Alzheimer's disease), condition or symptoms, and groups without the disease, condition or symptoms (e.g., non-demented controls). Another comparative group would be a group with a family history of a condition and a group without such a family history. The predetermined value can be arranged, for example, where a tested population is divided equally (or unequally) into groups, such as a low-risk group, a medium-risk group and a high-risk group or into quadrants or quintiles, the lowest-risk group being individuals with the highest amounts of antibodies that bind oxidized Aβ oligomers and the highest-risk group being individuals with the highest amounts of antibodies that bind oxidized Aβ oligomers. Appropriate ranges and categories can be selected with no more than routine experimentation by those of ordinary skill in the art. Typically the control will be based on apparently healthy normal individuals in an appropriate age bracket.

It will also be understood that the controls according to the invention may be, in addition to predetermined values, samples of materials tested in parallel with the experimental materials. Examples include samples from control populations or control samples generated through manufacture to be tested in parallel with the experimental samples.

The various assays used to determine the levels of antibodies include the assays described in the Examples section herein and other assays well known to one of ordinary skill in the art. Immunoassays may be used according to the invention including sandwich-type ELISA assays, competitive binding assays, one-step direct tests and two-step tests such as routinely practiced by those of ordinary skill in the art.

As mentioned above, it is also possible to characterize the existence of an Aβ accumulation-associated disorder by monitoring changes in the absolute or relative amounts of antibodies that bind oxidized Aβ oligomers over time. For example, it is expected that a decrease in the amount of antibodies that bind oxidized Aβ oligomers correlates with increasing severity of an Aβ accumulation-associated disorder. Accordingly one can monitor levels of antibodies that bind oxidized Aβ oligomers to determine if the status (e.g. severity, existence) of an Aβ accumulation-associated disorder of a subject is changing. Changes in relative or absolute levels of antibodies that bind oxidized Aβ oligomers of greater than 0.1% may indicate an abnormality. Preferably, the change in levels of antibodies that bind oxidized Aβ oligomers, which indicates an abnormality, is greater than 0.2%, greater than 0.5%, greater than 1.0%, 2.0%, 3.0%, 4.0%, 5.0%, 7.0%, 10%, 15%, 20%, 25%, 30%, 40%, 50%, or more. Other changes, (e.g. increases or reductions) in levels of antibodies that bind oxidized Aβ oligomers over time may indicate an onset, progression, regression, or remission of the Aβ accumulation-associated disorder in the subject. An increase in level of antibodies that bind oxidized Aβ oligomers may mean regression of the disorder. Such a regression may be associated with a clinical treatment of the disorder; thus, the methods of the invention can be used to determine the efficacy of a therapy for an Aβ-accumulation-associated disorder (e.g. Alzheimer's disease).

The invention in another aspect provides a diagnostic method to determine the effectiveness of treatments. The "evaluation of treatment" as used herein, means the comparison of a subject's levels of antibodies that bind oxidized Aβ oligomers measured in samples collected from the subject at different sample times, preferably at least one day apart. The preferred time to obtain the second sample from the subject is at least one day after obtaining the first sample, which means the second sample is obtained at any time following the day of the first sample collection, preferably at least 12, 18, 24, 36, 48 or more hours after the time of first sample collection. Days, weeks, months or even years can separate the collection of samples in time.

The comparison of levels of antibodies that bind oxidized Aβ oligomers in two or more samples, taken at different times, allows evaluation of the treatment to regulate levels of antibodies that bind oxidized Aβ oligomers. Such a comparison provides a measure of the status of the Aβ accumulation-associated disorder to determine the effectiveness of any treatment to regulate levels of antibodies that bind oxidized Aβ oligomers. These methods also permit determination of regression, progression or onset of disease.

In general, treatment methods involve administering an agent to increase the immune response to oxidized Aβ oligomers (e.g., CLAPS) and/or increase the level of antibodies to oxidized Aβ oligomers (e.g., through passive immunization).

Antibodies and/or antigen-binding fragments thereof, that selectively bind to oxidized Aβ oligomers, particularly CLAPS, are useful in diagnostic methods and therapeutic methods. As described herein, the antibodies of the present invention are prepared by any of a variety of methods, including administering protein, fragments of protein (e.g., CLAPS) and the like to an animal to induce polyclonal antibodies. The production of monoclonal antibodies is performed according to techniques well known in the art. As detailed herein, such antibodies or antigen-binding fragments thereof may be used for example to diagnose disease, monitor treatment, and for therapies including the prevention and treatment of Alzheimer's disease.

Thus isolated antibodies or antigen-binding fragments thereof can be identified and prepared that bind specifically to oxidized Aβ oligomers, particularly CLAPS. As used herein, "binding selectively to" means capable of distinguishing the identified material from other materials sufficient for the purpose to which the invention relates. Thus, "binding selectively to" or "selectively binds" an oxidized Aβ oligomer means the ability to bind to and distinguish these molecules from other Aβ molecules and oligomers. "Selectively binds" means that an antibody preferentially binds to an oxidized Aβ oligomer (e.g., with greater avidity, greater binding affinity) rather than to a non-oxidized Aβ oligomer or an Aβ monomer. In preferred embodiments, the antibodies of the invention bind to an oxidized Aβ oligomer with an avidity and/or binding affinity that is 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 7-fold, 10-fold, 20-fold, 30-fold, 40-fold, 50-fold, 70-fold, 100-fold, 200-fold, 300-fold, 500-fold, 1000-fold or more than that exhibited by the antibody for a non-oxidized Aβ oligomer or an Aβ monomer. Preferably, the antibody selectively binds an oxidized Aβ oligomer, and not a non-oxidized Aβ oligomer or an AD monomer, i.e., substantially exclusively binds to an oxidized Aβ oligomer. Most preferably, the antibody selectively binds a CLAPS molecule. Preferably the antibodies have binding affinity greater than or equal to about $10^6$, $10^7$, $10^8$, $10^9$, or $10^{10}$ M$^{-1}$.

Antibodies also may be coupled to specific diagnostic labeling agents for imaging of cells and tissues with oxidized Aβ oligomers; or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. Other diagnostic agents useful in the invention will be apparent to one of ordinary skill in the art.

As is well-known in the art, only a small portion of an antibody molecule, the paratope, is involved in the binding of the antibody to its epitope (see, in general, Clark, W. R. (1986) The Experimental Foundations of Modern Immunology, Wiley & Sons, Inc., New York; Roitt, I. (1991) Essential Immunology, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F9(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, W. R. (1986) The Experimental Foundations of Modern Immunology, Wiley & Sons, Inc., New York; Roitt, I. (1991) Essential Immunology, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "chimeric" and "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205, and references cited therein, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals results in the production of fully human antibodies to the antigen of interest. Following immunization of these mice (e.g., XenoMouse (Abgenix), HuMAb mice (Medarex/GenPharm)), monoclonal antibodies are prepared according to standard hybridoma technology. These monoclonal antibodies have human immunoglobulin amino acid sequences and therefore will not provoke human anti-mouse antibody (HAMA) responses when administered to humans.

Thus, as will be apparent to one of ordinary skill in the art, the present invention also provides for F(ab')2, Fab, Fv and Fd fragments; chimeric antibodies in which the Fc and/or Fr and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention involves polypeptides of numerous size and type that bind selectively to oxidized Aβ oligomers. These polypeptides may be derived also from sources other than antibody technology. For example, such polypeptide-binding agents can be provided by degenerate peptide libraries, which can be readily prepared in solution, in immobilized form or as phage display libraries. Combinatorial libraries also can be synthesized of peptides containing one or more amino acids. Libraries further can be synthesized of non-peptide synthetic moieties.

The antibodies described herein may be administered for therapeutic and/prophylactic uses. Although not wishing to be bound by any theory or mode of action, it is believed that the antibodies can bind to and decrease the accumulation of certain oxidized Aβ oligomers, with accompanying reduction of toxicity for the subject.

The oxidized Aβ oligomers, particularly CLAPS, can be prepared by oxidation of Aβ and its oligomers, or native species can be isolated from biological samples including blood, plasma, tissue or cell samples, etc. Oxidation of Aβ oligomers can be performed according to the method described in the Examples, or by any other suitable method known to one of ordinary skill in the art.

Thus, as used herein with respect to proteins, "isolated" means separated from its native environment and present in sufficient quantity to permit its identification or use. Isolated, when referring to a protein or polypeptide, means, for example: (i) selectively produced by expression of a recombinant nucleic acid, (ii) purified as by chromatography or electrophoresis or (iii) prepared by synthesis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure proteins may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, e.g. isolated from other proteins.

The prevention and treatment methods of the invention include administration of oxidized Aβ oligomers, to increase the immune response to these oligomers, particularly the level of antibodies that specifically bind to the oxidized Aβ oligomers. Methods for prevention and/or treatment also can include the administration to a subject of antibodies that specifically bind to the oxidized Aβ oligomers, e.g., CLAPS. The latter of these methods is typically called "passive immunization".

When administered, the therapeutic molecules of the present invention (including oxidized Aβ oligomers, particularly CLAPS; antibodies and fragments thereof) are administered in pharmaceutically acceptable preparations. Such preparations may routinely contain pharmaceutically acceptable concentrations of salt, buffering agents, preservatives, compatible carriers, and optionally other therapeutic agents.

The term "pharmaceutically acceptable" means a non-toxic material that does not interfere with the effectiveness of the biological activity of the active ingredients. The characteristics of the carrier will depend on the route of administration.

The therapeutics of the invention can be administered by any conventional route, including injection or by gradual infusion over time. The administration may, for example, be intravenous, intraperitoneal, intramuscular, oral, intranasal, intracavity, intrathecal, intracranial, subcutaneous, intradermal, or transdermal.

The therapeutic compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the therapeutic agent into association with a liquid carrier, a finely divided solid carrier, or both, and then, if necessary, shaping the product.

Compositions suitable for parenteral administration conveniently comprise a sterile aqueous preparation of the therapeutic agent, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol, Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Compositions suitable for oral administration may be presented as discrete units such as capsules, cachets, tablets, or lozenges, each containing a predetermined amount of the therapeutic agent. Other compositions include suspensions in aqueous liquors or non-aqueous liquids such as a syrup, an elixir, or an emulsion.

The invention provides a composition of the above-described agents for use as a medicament, methods for preparing the medicament and methods for the sustained release of the medicament in vivo. Delivery systems can include time-release, delayed release or sustained release delivery systems. Such systems can avoid repeated administrations of the therapeutic agent of the invention, increasing convenience to the subject and the physician. Many types of release delivery systems are available and known to those of ordinary skill in the art. They include polymer-based systems such as polylactic and polyglycolic acid, poly(lactide-glycolide), copolyoxalates, polyanhydrides, polyesteramides, polyorthoesters, polyhydroxybutyric acid, and polycaprolactone. Microcapsules of the foregoing polymers containing drugs are described in, for example, U.S. Pat. No. 5,075,109. Nonpolymer systems that are lipids including sterols such as cholesterol, cholesterol esters and fatty acids or neutral fats such as mono-, di- and tri-glycerides; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In one particular embodiment, the preferred vehicle is a biocompatible microparticle or implant that is suitable for implantation into the mammalian recipient. Exemplary bioerodible implants that are useful in accordance with this method are described in PCT International application no. PCT/US95/03307 (Publication No. WO 95/24929, entitled "Polymeric Gene Delivery System". PCT/US95/03307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the compound(s) of the invention is encapsulated or dispersed within the biocompatible, preferably biodegradable polymeric matrix disclosed in PCT/US95/03307. The polymeric matrix preferably is in the form of a microparticle such as a microsphere (wherein the compound is dispersed throughout a solid polymeric matrix) or a microcapsule (wherein the compound is stored in the core of a polymeric shell). Other forms of the polymeric matrix for containing the compounds of the invention include films, coatings, gels, implants, and stents. The size and composition of the polymeric matrix device is selected to result in favorable release kinetics in the tissue into which the matrix device is implanted. The size of the polymeric matrix device further is selected according to the method of delivery that is to be used. The polymeric matrix composition can be selected to have both favorable degradation rates and also to be formed of a material that is bioadhesive, to further increase the effectiveness of transfer when the devise is administered to a vascular surface. The matrix composition also can be selected not to degrade, but rather, to release by diffusion over an extended period of time.

Both non-biodegradable and biodegradable polymeric matrices can be used to deliver agents of the invention of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the agents of the invention are delivered using the bioerodible implant by way of diffusion, or more preferably, by degradation of the polymeric matrix. Exemplary synthetic polymers that can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein by reference, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Use of a long-term sustained release implant may be particularly suitable for treatment of established neurological disorder conditions as well as subjects at risk of developing a neurological disorder. "Long-term" release, as used herein, means that the implant is constructed and arranged to deliver therapeutic levels of the active ingredient for at least 7 days, and preferably 30-60 days. The implant may be positioned at or near the site of the neurological damage or the area of the brain or nervous system affected by or involved in the neurological disorder. Long-term sustained release implants are well known to those of ordinary skill in the art and include some of the release systems described above.

A response to a prophylatic and/or treatment method of the invention can be measured, for example, by determining the physiological effects of the treatment or medication, such as the decrease or lack of disease symptoms following administration of the treatment or pharmacological agent. Other assays will be known to one of ordinary skill in the art and can be employed for measuring the level of the response. For example, the behavioral and neurological diagnostic methods that are used to ascertain the likelihood that a subject has Alzheimer's disease, and to determine the putative stage of the disease can be used to ascertain the level of response to a prophylactic and/or treatment method of the invention. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount can depend upon the degree to which an individual has abnormal levels of antibodies to oxidized Aβ oligomers. In the case of passive immunization, treatment of those individuals having lower levels of antibodies or no measurable antibodies may require higher levels of antibodies to be administered.

The factors involved in determining an effective amount are well known to those of ordinary skill in the art and can be addressed with no more than routine experimentation. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

The therapeutically effective amount of a pharmacological agent of the invention is that amount effective to increase antibodies that selectively bind oxidized Aβ oligomers, and preferably reduce or prevent an Aβ accumulation-associated disorder, such as Alzheimer's disease.

In the case of treating a particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

The pharmaceutical compositions used in the foregoing methods preferably are sterile and contain an effective amount of a pharmacological agent for producing the desired response in a unit of weight or volume suitable for administration to a patient.

The doses of pharmacological agents administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent of the invention may be adjusted by the individual physician or veterinarian, particularly in the event of any complication. A therapeutically effective amount typically varies from 0.01 µg/kg to about 1000 mg/kg, preferably from about 1.0 µg/kg to about 200 mg/kg, and most preferably from about 0.1 mg/kg to about 10 mg/kg, in one or more dose administrations daily, for one or more days.

Various modes of administration will be known to one of ordinary skill in the art which effectively deliver the pharmacological agents of the invention to a desired tissue, cell, or bodily fluid. The administration methods include: topical, intravenous, oral, inhalation, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., Remington's Pharmaceutical Sciences, 18th edition, 1990) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration (e.g., intra-organ) and the like vary from those presented herein.

Administration of pharmacological agents of the invention to mammals other than humans, e.g. for testing purposes or veterinary therapeutic purposes, is carried out under substantially the same conditions as described above. It will be understood by one of ordinary skill in the art that this invention is applicable to both human and animal diseases including Aβ accumulation-associated disorders of the invention. Thus, this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the pharmacological agents and/or compositions of the invention.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride; chlorobutanol; parabens and thimerosal.

The invention will be more fully understood by reference to the following examples. These examples, however, are merely intended to illustrate the embodiments of the invention and are not to be construed to limit the scope of the invention.

EXAMPLES

Methods

AD and control cases. Plasma samples were collected from patients in the Memory and Movement Disorders Unit of Massachusetts General Hospital (MGH) in Boston, Mass. following informed consent. Samples were collected as part of a biomarker study approved by the MGH Institutional Review Board. Participants had a diagnoses of AD (n=59) by NINCDS-ADRDA criteria[27] or non-demented controls (n=59). The demographics of the population are shown in Table 1.

TABLE 1

Demographic and biochemical data on non-demented control and AD cohorts.
The table shows age, duration of illness and education as average years ± standard deviation (SD) for non-demented control and AD cohorts. Aβ40 and Aβ42 plasma levels were determined by sandwich ELISA and are shown as average concentrations (picomolar) ± SD.

|  | Control | AD |
|---|---|---|
| Demographic Data |  |  |
| n | 59 |  |
| Age (y) | 70 ± 10 | 77 ± 8 |
| % Male | 44 |  |
| Duration of AD (y) |  | 5 ± 3.3 |
| Education (y) | 15 ± 3.2 | 13 ± 3.1 |
| Biochemical Data |  |  |
| Aβ40 (pM) | 45 ± 14 | 50 ± 18 |
| Aβ42 (pM) | 6.2 ± 2.7 | 6.4 ± 2.8 |

Preparation of stock Solutions and Buffers. Stock Aβ Solutions were Prepared by Addition of 30% trifluoroethanol in HPLC grade water to ≈1 mg of powdered Aβ40 (synthesized by the W. Keck Laboratory, Yale University, New Haven). Undissolved peptide was solubilized by light sonication of the stock solution for 3 minutes. Following sonication, the Aβ solution was centrifuged to remove undissolved material and peptide concentration in the supernatant determined by Bicinchoninic acid protein assay (Pierce, Rockford Ill.). Zn(II)-histidine buffers were prepared by combining zinc standard solution (National Institute of Standards and Technology) with TBS (150 mM NaCl in 50 mM Tris, pH 7.4) containing histidine for a final Zn(II):histidine molar ratio of 1:6.

HRP treatment of Aβ. The method first described by Galeazzi et al (1999)[28] was used to generated cross-linked β-amyloid protein species (CLAPS). Fresh Aβ40 (100 μg/ml) was incubated (2 days at 37° C.) in TBS with 10 μg/ml horse radish peroxidase (HRP) in the presence of hydrogen peroxide (100 μM). Following incubation, HRP in the sample was inactivated by incubation (1 hr at 37° C.) with sodium azide (5%), an irreversible inhibitor of peroxidase activity. No peroxidase signal was detected in solutions of, or microplate wells coated with, HRP-treated Aβ (data not shown). Aβ oligomerization during incubation with HRP was monitored by Western blot using a polyclonal antibody (pAb) pan Aβ raised against full-length peptide (Calbiochem, San Diego, Calif.).

Aβ antibody ELISA. Aβ was first immobilized to the solid phase. Unmodified or HRP-treated peptide (100 μg/ml) was incubated in TBS (20 μl/well) in the wells of a 384-well microplate. For some experiments unmodified Aβ was incubated in wells containing 100 μM Zn(II)-histidine buffer. Following the capture step, plates were blocked overnight at 4° C. with BSA/TBS buffer (10% BSA in TBS). Wells were then incubated with plasma samples diluted 1:50 in BSA/TBS buffer. After washing, wells were incubated with a 1:25,000 dilution of goat anti-IgG antibody conjugated to HRP (Calbiochem, San Diego Calif.). The plate was washed and luminescence measured after addition of 20 μl/well of luminol solution (Pierce, Rockford Ill.).

Immunoblotting (Western blotting). Samples were first resolved by electrophoresis on SDS-PAGE (4-12% Bis-Tris gels) and then transferred to nitrocellulose membrane. Membranes were blocked overnight at 4° C. with TBST containing 5% each of skimmed milk and BSA. For detection of Aβ, membranes were first probed (2 hrs at room temperature) with 1:3000 dilution of pAb pan Aβ, then incubated with goat anti-rabbit IgG-coupled to HRP (1:10000). For detection of Aβ immunoreactivity in human plasma, membranes blotted with Aβ were incubated (overnight at 4° C.) with plasma samples diluted 1:100 in BSA/TBST. Membranes were then washed and probed with anti-human-IgG-HRP conjugate. Both Aβ detection and Aβ immunoreactivity blots were developed for exposure to enhanced chemiluminescence (ECL)-film with super signal ultra (Pierce, Rockford Ill.).

IgG ELISA. Plasma samples and standards of known IgG concentration were diluted (1:20) in BSA/TBS buffer and incubated (1 hr at room temp) in fresh untreated microplate wells. Following washing, wells were probed (1 hr at room temperature) with anti-IgG-HRP conjugated antibody (1:50,000) in BSA/TBS. Well chemiluminescence was then measured following addition of luminol.

Aβ40 and Aβ42 plasma levels. Plasma levels of Aβ40 and Aβ42 were determined by sandwich ELISA as described by Fukumoto et al., (2003)[29]. Briefly, Aβ was captured to the solid phase using an antibody directed against residues 11-28 of the peptide (anti-Aβ11-28). Bound Aβ was detected using anti-Aβ antibodies 1BA27 (Aβ40 specific) or BC05 (Aβ42 specific). The three antibodies were obtained from Takeda Chemical Industries, Osaka, Japan.

Results

Figure 1B:
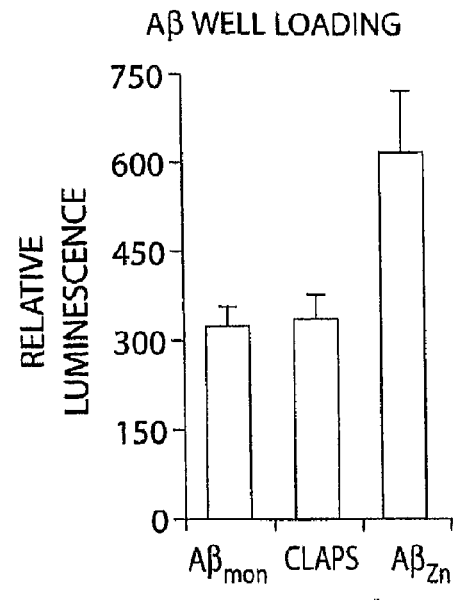
FIG. 1b: Efficiency of solid phase capture of unmodified Aβ, peptide pre-treated with HRP, and Aβ incubated in Zn(II)-histidine buffer. Wells were incubated with TBS containing normal Aβ (Aβ$_{mon}$) or peptide pre-treated with HRP (CLAPS). Wells were also incubated with normal Aβ in Zn(II)-histidine buffer (Aβ$_{Zn}$). Following the capture step wells were probed with pan Aβ. Bound antibodies were detected with anti-rabbit-HRP conjugate. Well loading for unmodified and HRP-treated Aβ differed by <3%. Consistent with metal-induced Aβ aggregation, peptide capture was elevated in the presence of zinc.

We first established an ELISA to measure titers of anti-Aβ autoantibodies in human plasma. Initial experiments characterized the Aβ species used to capture autoantibodies from plasma. Wells were coated with either unmodified monomeric Aβ ($A\beta_{mon}$), HRP-treated peptide containing cross-linked β-amyloid protein species (CLAPS), or peptide assembled into non-covalent multimers by incubation with Zn(II)/histidine ($A\beta_{Zn}$). The wells were then extracted with SDS sample buffer and the extracts immunoblotted using a polyclonal (pAb) antibody raised against full-length Aβ peptide (pan Aβ). Analysis of immunoblot signal confirmed that the wells contained immobilized Aβ (FIG. 1a). Untreated Aβ and peptide immobilized in the presence of Zn(II)-histidine were monomeric. However, HRP-treated peptide contained additional cross-linked oligomeric species. We next compared wells for peptide loading. Following incubation with Aβ preparations, the wells were blocked and then incubated with pAb pan Aβ. Bound antibody was detected by addition of chemiluminescence reagent following incubation with goat anti-rabbit IgG-coupled to HRP (FIG. 1b). Aβ loading for wells incubated with unmodified versus HRP-treated peptide differed on average by <3%. Signal strength was also similar between replicate wells within a range of <9% of total loading. Consistent with the formation and capture of aggregated Aβ assemblies, wells contained almost 2-fold more peptide when incubations included Zn(II)-histidine buffer.

Figure 1C:
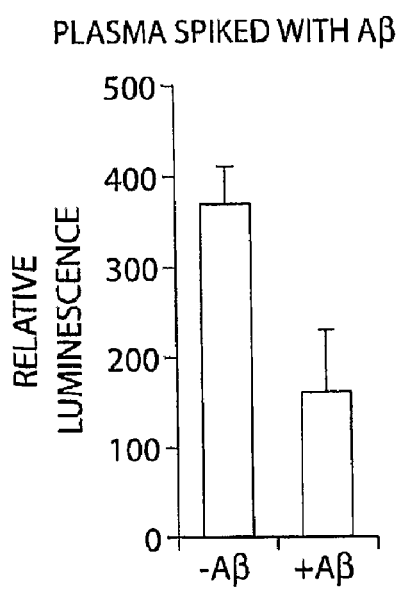
FIG. 1c: Anti-Aβ signal is attenuated by pre-absorption with synthetic Aβ peptide. Non-demented control plasma was pre-incubated±soluble unmodified Aβ (1 µg/ml). Plasma incubants were then assayed by anti-Aβ ELISA. Consistent with specificity of our ELISA for anti-Aβ autoantibodies, signal was reduced for plasma samples containing soluble synthetic peptide.
Figure 1D:
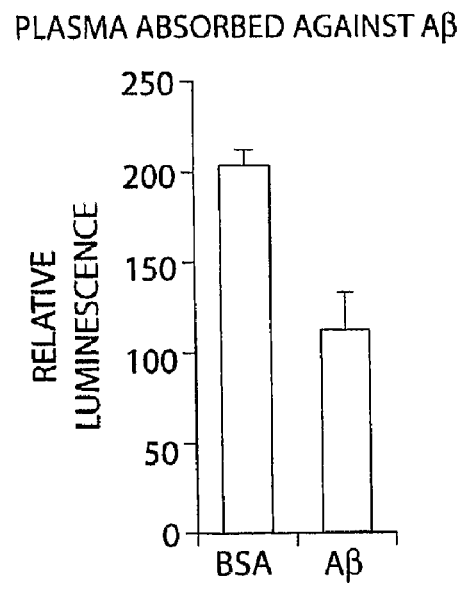
FIG. 1d: Signal for anti-Aβ antibodies is attenuated by pre-incubation of plasma with immobilized Aβ. Non-demented control plasma was pre-incubated in wells coated with BSA or immobilized Aβ peptide. Plasma incubants were then removed and assayed for anti-Aβ immunoreactivity. Consistent with depletion of anti-Aβ antibodies and specificity of our ELISA, signal was reduced for plasma pre-incubated with immobilized Aβ. All experiments used 384-well plates. Well signal was determined from luminescence following addition of chemiluminescent reagent. Anti-Aβ ELISA data is shown as average of 8 replicates±standard error.

Next we tested the specificity of the ELISA for anti-Aβ immunoreactivity. Non-demented control plasma was pre-incubated (30 minutes) with either BSA or exogenous soluble $A\beta_{mon}$ (final concentration in well of 1 μg/ml) before being assayed. In a complementary experiment, plasma was pre-incubated in wells coated with BSA or immobilized $A\beta_{mon}$, removed and then assayed for anti-Aβ immunoreactivity. Consistent with specificity for anti-Aβ immunoreactivity, signal was reduced relative to BSA pre-incubations for both anti-Aβ antibody absorption (FIG. 1c) and depletion (FIG. 1d) experiments. Notably, for the absorption experiments (FIG. 1c) no detectable attenuation of signal was observed for plasma spiked with <100 ng/ml of exogenous Aβ (data not shown). Previous studies have suggested that the total pool of Aβ in undiluted human plasma is <5 ng/ml[29-33]. In addition, plasma samples are diluted 50-fold prior to assay. Thus, endogenous Aβ is unlikely to significantly reduce assay signal by competing with immobilized peptide for autoantibody binding.

The 42 residue isoform of Aβ was also tested in our ELISA. However, we were unable to reproducibly coat replicate wells with equivalent loadings of HRP or metal-treated Aβ42 peptide (data not shown). This was due to the greater propensity of Aβ42 to aggregate as compared to the less hydrophobic 40 amino acid isoform. Therefore, Aβ42 was not used in the experiments in this study.

Figure 2A:
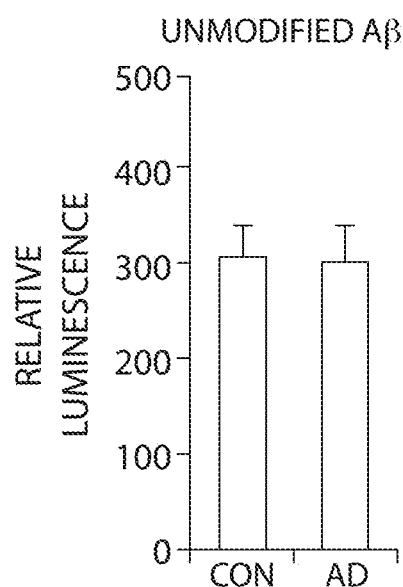
FIG. 2: AD plasma has significantly reduced autoimmunity for redox cross-linked Aβ oligomers as compared to non-demented controls. Wells were coated with BSA, or Aβ that was unmodified (FIG. 2a), pre-treated with HRP (FIG. 2b) or captured in Zn(II)-histidine buffer (FIG. 2c). Following blocking, wells were incubated with plasma from AD (n=59) or non-demented control (n=59) cases. Bound antibodies were detected by incubation with anti-IgG-HRP conjugate. Control plasma autoimmunity to HRP-treated Aβ was significantly elevated (*p=0.028 by 2-tailed student t-test) compared to AD samples. Plasmas were also compared for IgG levels (FIG. 2d). Diluted plasma and IgG standards were captured to the solid phase by incubation in fresh microplate wells. Immobilized IgG was detected with anti-IgG-HRP antibody conjugate. No significant difference in IgG concentration was observed between AD and control cohorts. All assays used 384-well plates. Well signal was determined from luminescence following addition of Luminol. Signal from Aβ containing wells was blanked on signal from wells pre-incubated with BSA. Data is shown as average sample signal (16 replicates for each plasma sample) for each test group±standard error.
Figure 2B:
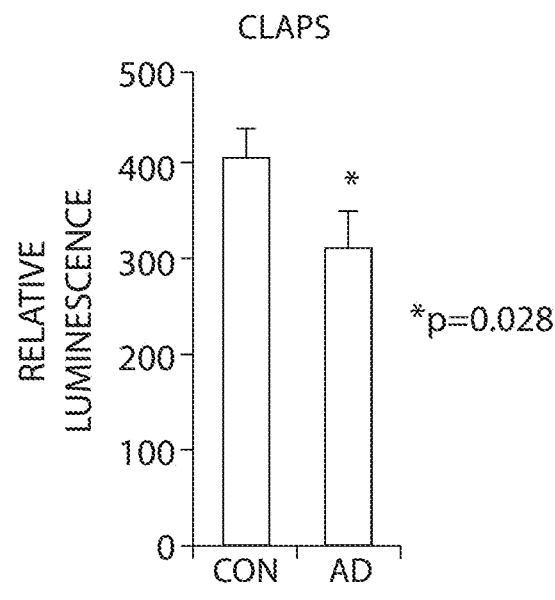
Figure 2C:
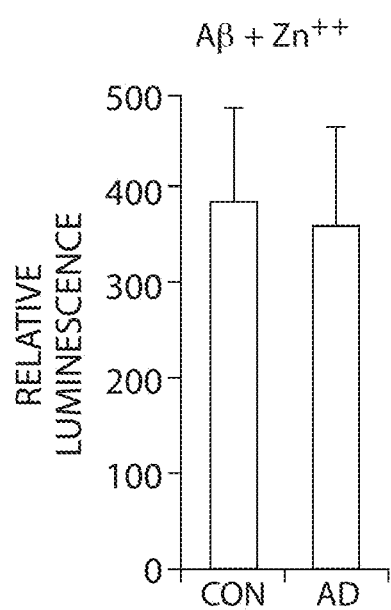

Following assay characterization experiments, control (n=59) and AD (n=59) plasma were compared for immunoreactivity to either unmodified Aβ ($A\beta_{mon}$), Zn-treated Aβ ($A\beta_{Zn}$), or cross-linked Aβ (CLAPS). Wells were incubated with the various Aβ preparations, blocked, incubated with samples of diluted (1:50) plasma, and then probed for bound human IgG (FIG. 2). No significant difference was found between control and AD immunoreactivity to $A\beta_{mon}$ or $A\beta_{Zn}$ aggregates (FIG. 2a and FIG. 2c). However, signal from control plasma incubated with CLAPS was significantly elevated (p=0.028 by t-test) as compared to AD samples (FIG. 2b). In addition, the immunoreactivity of plasma from non-demented patients was greater for CLAPS than for $A\beta_{mon}$. Differences in well loading precluded direct comparison of signals from wells containing zinc-treated peptide versus those coated with unmodified or cross-linked Aβ.

Figure 2D:
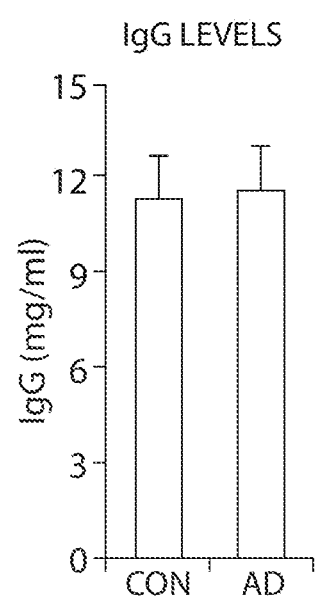

In a control experiment, plasma from control and AD cases were also assayed for total IgG levels. Consistent with previous studies of plasma[25, 34, 35] and CSF[36], no significant differences were found between control and AD plasma IgG concentrations (FIG. 2d). Thus, the reduced levels of anti-CLAPS antibodies we observed for AD plasma cannot be attributed to a non-specific decline in circulating IgG concentrations.

Figure 3:
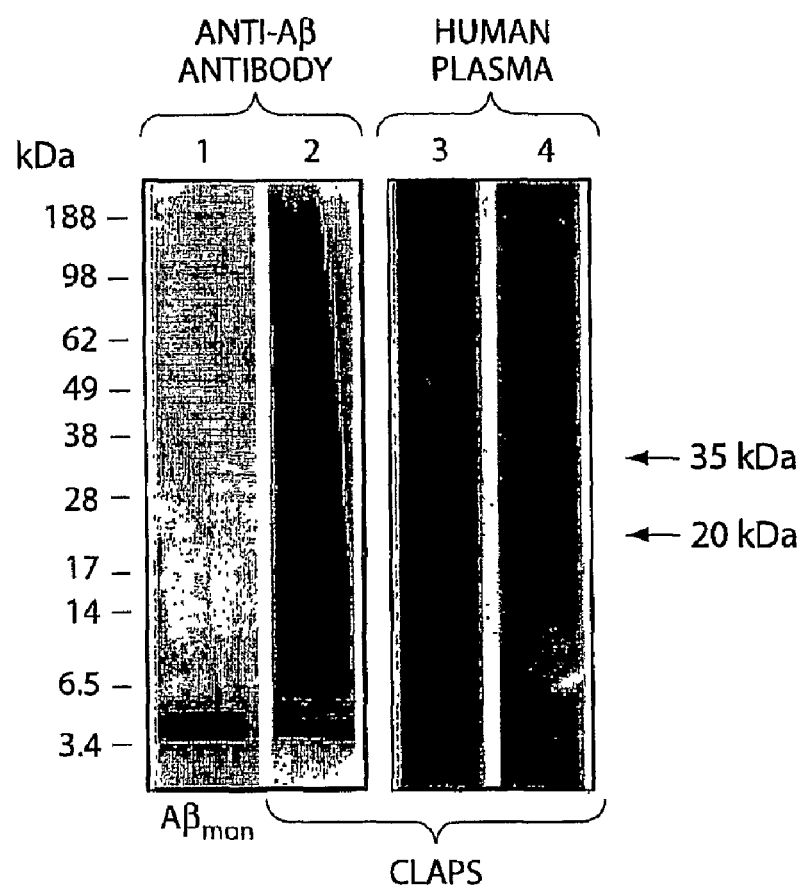
FIG. 3: Antibodies from human plasma bind redox cross-linked Aβ species (CLAPS) resolved by SDS-PAGE and blotted to nitrocellulose membrane. Unmodified Aβ (Aβ$_{mon}$, lane 1) and peptide pre-treated with HRP (CLAPS, lanes 2, 3 and 4) were resolved on SDS-PAGE and transferred to nitrocellulose membrane. Blots were incubated with pAb pan Aβ (lanes 1 and 2) or diluted (1:100) human plasma from two non-demented patients (lanes 3 and 4) previously identified by Aβ autoimmunity ELISA to have high antibody titers to HRP-treated Aβ. Blots were incubated with anti-rabbit or anti-human-HRP conjugated antibodies and developed for exposure to ECL-film. Signal was highest for species with apparent molecular weights corresponding to Aβ oligomers containing between four and eight cross-linked monomeric units.

Next, immunoblotting techniques were used to characterize the immunogenicity of human plasma to CLAPS. For these experiments, HRP-treated Aβ was resolved by SDS-PAGE and transferred to nitrocellulose membrane. Membranes were then incubated with diluted plasma (1:100 in 10% BSA in TBST) and probed with goat anti-IgG-HRP conjugated antibody. When immunoreactivity was detected in plasma from non-demented controls, the signal was highest for species with apparent molecular weights of 15-35 kDa (FIG. 3). However, the sensitivity of the immunoblot assay was insufficient for discrete detection of anti-Aβ immunoreactivity in most samples in our cohort. Notably, the two samples presented in FIG. 3 that generated clear signals by immunoblot assay also possessed the highest anti-CLAPS titers by ELISA.

Next, we compared anti-CLAPS antibody titers to levels of soluble Aβ in plasma as determined by sandwich ELISA. Anti-CLAPS antibody titers did not correlate significantly with either Aβ40 or Aβ42 concentrations or Aβ42/Aβ40 ratio in control, AD, or the combined plasma samples (Table 2). However plasma immunoreactivity to CLAPS was found to correlate positively (r=0.267 with p=0.041) with the age-at-onset (AAO) of AD: the earlier the AAO, the lower plasma immunoreactivity towards CLAPS. AD plasma antibody titers for $A\beta_{mon}$ also demonstrated a trend toward positive correlation with AAO but did not reach statistical significance (p=0.118). We also detected a trend in which plasma anti-CLAPS immunoreactivity was decreased as a function of he progression of AD, but this did not reach statistical significance (r=−0.209 with p=0.111). Additional studies with larger cohorts will be required to determine whether these two latter trends can be authenticated.

TABLE 2

Autoimmunoreactivity signal correlates with age of onset of AD but not plasma Aβ levels.
The nonparametric correlation coefficient (Spearman rank) and p value (2-tailed) was
calculated for immunoreactivity to unmodified (Aβ$_{mon}$) or HRP-generated cross-linked
β-amyloid protein species (CLAPS) and corresponding plasma levels of Aβ40 or Aβ42 or
Aβ40/Aβ42 ratio. Analysis tested control, and AD cohorts separately and combined.
Plasma Aβ isoform levels were determined by sandwich ELISA. For the AD cohort,
plasma immunoreactivity was also tested against age-at-onset (AAO) and duration (years
from first positive diagnoses to sample collection) of AD. Consistent with previous
analysis, AAO for AD was found to correlate (p = 0.041*) with plasma immunoreactivity
to HRP-treated Aβ. While the trend did not reach significance (p = 0.11), plasma
immunoreactivity to HRP-treated Aβ also demonstrated a trend toward negative correlation
with the number of years patients had displayed clinical AD symptoms.

|  | Control | | AD | | Combined | |
| --- | --- | --- | --- | --- | --- | --- |
|  | Aβ$_{mon}$ | CLAPS | Aβ$_{mon}$ | CLAPS | Aβ$_{mon}$ | CLAPS |
| Aβ40 | r = 0.008 | r = 0.072 | r = −0.05 | r = 0.123 | r = 0.008 | r = 0.091 |
|  | p = 0.531 | p = 0.584 | p = 0.691 | p = 0.324 | p = 0.933 | p = 0.327 |
| Aβ42 | r = 0.110 | r = 0.096 | r = 0.078 | r = 0.074 | r = 0.028 | r = 0.023 |
|  | p = 0.401 | p = 0.468 | p = 0.553 | p = 0.572 | p = 0.756 | p = 0.805 |
| Aβ40/Aβ42 | r = 0.012 | r = 0.003 | r = 0.141 | r = 0.061 | r = 0.023 | r = −0.023 |
|  | p = 0.923 | p = 0.982 | p = 0.281 | p = 0.644 | p = 0.801 | p = 0.800 |
| AD Onset Age | — | — | r = 0.196 | r = 0.279 | — | — |
|  | — | — | p = 0.136 | p = 0.041* | — | — |
| Disease Duration | — | — | r = −0.118 | r = −0.209 | — | — |
|  | — | — | p = 0.373 | p = 0.111 | — | — |

Discussion

Experiments with AD transgenic animal models suggest autoantibodies may have an important role in Aβ clearance[14-16]. However, while immunoreactivity of human plasma to Aβ$_{mon}$ has been previously investigated[23-26, 37], this is the first report of autoimmunity specific to the subpopulation of cross-linked Aβ that we refer to as "CLAPS". Our findings show that plasma from elderly non-demented control patients contain autoantibodies specific for CLAPS, in addition to immunoreactivity to unmodified Aβ. Furthermore, we report that immunoreactivity to CLAPS is significantly reduced in AD plasma as compared to non-demented controls and this reduction correlates with AAO of the disease. Data has been steadily accumulating to indicate that CLAPS have may have an important role in AD neuropathogenesis. Aβ neurotoxicity appears to be greatly potentiated when the peptide self-associates into organized structures. Recent data also suggest the proximal effectors of Aβ neurotoxicity may be the intermediates of fibril assembly[12, 13], particularly dimeric and trimeric CLAPS[38]. Consistent with the potentially important pathological role for CLAPS, the protofibrils of other amyloid-forming proteins have also been shown to induce cell death, including α-synuclein, Huntingtin and PrP[11].

Antibodies to Aβ appear to develop in both non-demented and AD patients[21, 22, 24-26, 37] and are most likely a part of normal aging. Circulating levels of autoantibodies generally increase with aging in accord with at least two mechanisms (see review by Weksler et al., 2002[39]). First, production of neo-antigens increase with age in response to general increases in protein oxidation, the accumulation of aggregated proteinaceous material, and subtle shifts in posttranslational possessing, most notably glycosylation. Second, while levels of neo-antigens increase with age, the diversity of the general antibody repertoire steadily declines. This leads to an increase in the concentration of B-cell clonal idiotypes, eventually stimulating production of anti-idiotypic autoantibodies. Several previous studies have evaluated AD and age-matched control plasma for potential differences in the levels of anti-Aβ autoantibodies. However, the collective findings have been contradictory with an elevation 23, a decrease[24, 25], and no change[26] reported for levels of anti-Aβ antibodies in the plasma of AD cases versus non-demented controls.

Our data are consistent with previous reports, at least with regard to our observation of equivalent levels of autoantibodies to unmodified Aβ in AD and non-demented control plasma samples[26] (FIG. 2a). However, control plasma contained additional immunoreactivity to oxidized Aβ species (FIG. 2). These data demonstrate that control plasma contains antibodies that recognize epitopes specific to oxidized forms of the peptide. In contrast, AD plasma samples contained much less immunoreactivity to oxidized Aβ. Our analysis also showed that anti-CLAPS antibody titers correlated significantly with AAO for AD (Table 2). Reduced anti-CLAPS immunoreactivity in AD plasma suggest that autoantibodies to CLAPS may be protective for AD. One possibility is that anti-CLAPS antibodies may aid in the clearance of these oxidized forms of Aβ or attenuate their neurotoxicity by binding to the oligomer structures[40].

Our experiments employed heterogeneous CLAPS preparations containing monomeric, dimeric, and multimeric cross-linked oligomers (FIG. 1a). Western blot assays were not sufficiently sensitive to conclusively quantitate the relative immunoreactivity of these different CLAPS for most samples in our cohort. However, our Western blot analysis was able to identify Aβ oligomers with apparent molecular weights (15-35 kDa) corresponding to between four and eight cross-linked monomeric units as the species with the highest immunoreactivity in our CLAPS preparations in control plasma (FIG. 3). Interestingly however, these were not the most abundant Aβ oligomers in our CLAP preparations (FIG. 1a). It is unclear what structural features render the (15-35 kDa) CLAPS relatively high apparent immunogenicity. The relative toxicity of different CLAPS species is also unclear. Recent studies have demonstrated that Aβ$_{mon}$ is substantially less neurotoxic than either cross-linked dimers[12, 13] or SDS-stable oligomers of between four and ten subunits (referred to as ADDLs)[13, 41]. While it remains to be determined whether the autoimmunogenicity and neurotoxicity of CLAPS are linked, our data are consistent with high immunoreactivity for the redox cross-linked oligomers, which have thus far been reported to be highly neurotoxic[12, 13,13, 41]. Thus, further characterization of the immunoreactive groups of CLAPS may be potentially useful for treatment strategies employing Aβ vaccination to reduce amyloid burden in AD patients. Our data are consistent with the prediction that an immunogen incorporating the autoimmunogenic structural features of 15-35 kDa redox-modified Aβ oligomers may increase the specificity of antibodies for pathologically relevant Aβ species, and thus represent a more effective immunization based therapeutic strategy for treating and preventing AD.

At least two populations of autoantibodies are likely to react with the CLAPS used in our assay. Redox modified Aβ from brain and peptide oxidized in vitro contain a number of chemical modifications, including isomerization[42, 43], carbonylation[44], and amino acid oxidation[45], while monomeric units in SDS-stable oligomeric species appear to be cross-linked by dityrosine bridges[28, 46, 47]. The chemical modifications observed for CLAPS are common to many oxidized proteins and are known to be epitopes for so-called natural autoantibodies (NAA)[48, 49]. NAA are characterized by broad reactivity directed against very well conserved public epitopes[39, 48, 49]. It is highly possible that a portion of anti-CLAPS immunoreactivity is mediated by NAA. Consistent with this posit, many of the anti-Aβ antibodies secreted by EBV-transformed B cells are polyreactive[50]. However, in addition to public epitopes, the secondary/tertiary conformation of cross-linked CLAPS oligomers may also generate neo-antigenic epitopes, and autoantibodies to these epitopes are likely to be much more specific for redox modified Aβ.

AD plasma possessed significantly less immunoreactivity to CLAPS than did control samples. It is unclear if the increased immunoreactivity in control plasma is directed against specific or public epitopes on CLAPS. Notably, control and AD plasma have exhibited equivalent immunoreactivity to zinc-generated Aβ assemblies (FIG. 2b). In the presence of zinc, Aβ self-associates into aggregates with an ordered structure that mimics many of the physiochemical properties of β-amyloid[51, 52]. However, zinc-treatment does not oxidize or covalently cross-link Aβ monomers (FIG. 1a). Thus, while the identity of the epitopes remain unclear, our findings suggest that the elevated levels of anti-CLAPS immunoreactivity in control plasma is specific for oxidized cross-linked oligomers and most likely not elicited by non-covalently bound assemblies of Aβ such as the aggregates that form in the presence of zinc.

It remains unclear whether AD patients have a low autoimmune response to CLAPS before the onset of the disease, or AD pathogenesis involves attenuation of anti-CLAPS antibody titers. AD pathogenesis may lower anti-CLAPS antibody titers via several mechanisms. AD patients may develop increased immunotolerance to CLAPS after the onset of the disease, possibly in response to elevated levels of redox-modified Aβ species. Elevated levels of circulating CLAPS may also act to deplete the pool of anti-CLAPS antibodies as antigen/antibody complexes are cleared from plasma. Unfortunately, direct determination of levels of specific forms of CLAPS in human plasma must await the development of assays specific for various redox-modified forms of the peptide. It is also possible that the pool of circulating anti-CLAPS antibodies in plasma may be depleted by absorption to insoluble β-amyloid deposits that line the cerebral vasculature of AD patients[53]. Recent findings from human Aβ vaccination trials confirm that β-amyloid in cerebral vasculature can provide a peripheral sink for anti-Aβ antibodies[17]. The ELISA used to measure anti-CLAPS immunoreactivity may also report artifactually low titers if anti-CLAPS antibodies were absorbed by elevated levels of plasma CLAPS. However, our ELISA characterization experiments (FIG. 1c) suggest that to significantly reduce anti-Aβ antibody capture under the conditions of our assay would require CLAPS concentrations 500-fold higher than the levels previously reported for soluble Aβ species in plasma[29-33]. Thus, it seems unlikely that elevated endogenous CLAPS levels are responsible for the attenuated signal observed for AD plasma.

Finally, it remains to be determined whether reduced levels of anti-CLAPS antibodies represent a risk factor for the development or progression of AD pathology. It is possible that anti-CLAPS autoantibodies may protect neurons by aiding in the clearance of these neurotoxic species or by neutralizing their bioactivity[40]. If this proves to be the case, then the efficacy of Aβ immunization and anti-Aβ passive infusion therapies might be enhanced by targeting oxidized Aβ species. Previous immunization trials have used only unmodified Aβ as the immunogenic agent. Recent findings are consistent with the posit that targeting specific epitopes on Aβ may improve treatment efficacy and reduce undesirable inflammatory responses[19].

In conclusion, our findings demonstrate that redox cross-linked oligomeric Aβ species are immunoreactive with human plasma. The immunoreactivity is specific for cross-linked oligomers, but not Aβ assemblies bound by non-covalent forces such as those found in zinc-induced Aβ aggregates. We also observed that AD plasma contained lower titers of anti-CLAPS antibodies compared to non-demented control subjects and that immunoreactivity to CLAPS correlated with AAO of the disease. These findings may be useful in revising and facilitating future designs of reagents for Aβ vaccination and passive antibody perfusion therapies aimed at treating and presenting AD.

REFERENCES

1. Citron M, Haass C, Selkoe D J. Production of amyloid-β-peptide by cultured cells: no evidence for internal initiation of translation at Met596. Neurobiol Aging. 1993; 14:571-573
2. Tanzi R E, Gusella J F, Watkins P C et al. Amyloid β protein gene: cDNA, mRNA distribution, and genetic linkage near the Alzheimer locus. Science 1987; 235:880-884
3. Kang J, Lemaire H G, Unterbeck A et al. The precursor of Alzheimer's disease amyloid A4 protein resembles a cell-surface receptor. Nature 1987; 325:733-736
4. Haass C, Schlossmacher M G, Hung A Y et al. Amyloid β-peptide is produced by cultured cells during normal metabolism [see comments]. Nature 1992; 359:322-325
5. Shoji M, Golde T E, Ghiso J et al. Production of the Alzheimer amyloid β protein by normal proteolytic processing. Science. 1992; 258:126-129
6. Seubert P, Vigo-Pelfrey C, Esch F et al. Isolation and quantification of soluble Alzheimer's β-peptide from biological fluids [see comments]. Nature 1992; 359:325-327
7. Suzuki N, Iwatsubo T, Odaka A et al. High tissue content of soluble β 1-40 is linked to cerebral amyloid angiopathy. Am J Pathol 1994; 145:452-460
8. Gravina S A, Ho L, Eckman C B et al. Amyloid β protein (Aβ) in Alzheimer's disease brain. Biochemical and immunocytochemical analysis with antibodies specific for forms ending at Aβ40 or Aβ42(43). J Biol Chem 1995; 270:7013-7016
9. Roher A E, Chaney M O, Kuo Y M et al. Morphology and toxicity of Aβ-(1-42) dimer derived from neuritic and vascular amyloid deposits of Alzheimer's disease. J Biol. Chem. 1996; 271:20631-20635

10. Bush A I, Tanzi R E. The galvanization of beta-amyloid in Alzheimer's disease. Proc Natl Acad Sci USA. 2002; 99:7317-7319

11. Caughey B, Lansbury P T. Protofibrils, pores, fibrils, and neurodegeneration: separating the responsible protein aggregates from the innocent bystanders. Annu Rev Neurosci. 2003; 26:267-298

12. Walsh D M, Tseng B P, Rydel R E et al. The oligomerization of amyloid beta-protein begins intracellularly in cells derived from human brain. Biochemistry. 2000; 39:10831-10839

13. Gong Y, Chang L, Viola K L et al. Alzheimer's disease-affected brain: presence of oligomeric A beta ligands (ADDLs) suggests a molecular basis for reversible memory loss. Proc Natl Acad Sci USA. 2003; 100:10417-10422

14. Schenk D, Barbour R, Dunn W et al. Immunization with amyloid-beta attenuates Alzheimer-disease-like pathology in the PDAPP mouse [see comments]. Nature. 1999; 400:173-177

15. Games D, Bard F, Grajeda H et al. Prevention and reduction of AD-type pathology in PDAPP mice immunized with A beta 1-42. Ann N Y Acad. Sci. 2000; 920:274-284

16. Bard F, Cannon C, Barbour R et al. Peripherally administered antibodies against amyloid beta-peptide enter the central nervous system and reduce pathology in a mouse model of Alzheimer disease. Nat. Med. 2000; 6:916-919

17. DeMattos R B, Bales K R, Cummins D J et al. Brain to plasma amyloid-beta efflux: a measure of brain amyloid burden in a mouse model of Alzheimer's disease. Science. 2002; 295:2264-2267

18. Matsuoka Y, Saito M, LaFrancois J et al. Novel therapeutic approach for the treatment of Alzheimer's disease by peripheral administration of agents with an affinity to beta-amyloid. J. Neurosci. 2003; 23:29-33

19. Bard F, Barbour R, Cannon C et al. Epitope and isotype specificities of antibodies to beta-amyloid peptide for protection against Alzheimer's disease-like neuropathology. Proc Natl Acad Sci USA. 2003; 100:2023-2028

20. Hock C, Konietzko U, Papassotiropoulos A et al. Generation of antibodies specific for beta-amyloid by vaccination of patients with Alzheimer disease. Nat. Med. 2002; 8:1270-1275

21. Mönning U, Schreiter-Gasser U, C. H et al. Alzheimer amyloid β-A4 protein-reactive antibodies in human sera and CSF in Alzheimers disease. In: Wisniewski H W, ed. Basic Mechanisms, Diagnosis and Therapeutic Strategies. New York: Wiley, 1991:557-563

22. Gaskin F, Finley J, Fang Q et al. Human antibodies reactive with β-amyloid protein in Alzheimer's disease. J Exp Med 1993; 177:1181-1186

23. Nath A, Hall E, Tuzova M et al. Autoantibodies to amyloid beta-peptide (Abeta) are increased in Alzheimer's disease patients and Abeta antibodies can enhance Abeta neurotoxicity: implications for disease pathogenesis and vaccine development. Neuromolecular Med. 2003; 3:29-39

24. Du Y, Dodel R, Hampel H et al. Reduced levels of amyloid beta-peptide antibody in Alzheimer disease. Neurology. 2001; 57:801-805

25. Weksler M E, Relkin N, Turkenich R et al. Patients with Alzheimer disease have lower levels of serum anti-amyloid peptide antibodies than healthy elderly individuals. Exp Gerontol. 2002; 37:943-948

26. Hyman B T, Smith C, Buldyrev I et al. Autoantibodies to amyloid-beta and Alzheimer's disease. Ann Neurol. 2001; 49:808-810

27. McKhann G, Drachman D, Folstein M et al. Clinical diagnosis of Alzheimer's disease: report of the NINCDS-ADRDA Work Group under the auspices of Department of Health and Human Services Task Force on Alzheimer's Disease. Neurology. 1984; 34:939-944

28. Galeazzi L, Ronchi P, Franceschi C, Giunta S. In vitro peroxidase oxidation induces stable dimers of β-amyloid (1-42) through dityrosine bridge formation. Amyloid. 1999; 6:7-13

29. Fukumoto H, Tennis M, Locascio J J et al. Age but not diagnosis is the main predictor of plasma amyloid beta-protein levels. Arch Neurol. 2003; 60:958-964

30. Mehta P D, Dalton A J, Mehta S P et al. Increased plasma amyloid β protein 1-42 levels in Down syndrome. Neurosci Lett. 1998; 241:13-16

31. Iwatsubo T. Amyloid β protein in plasma as a diagnostic marker for Alzheimer's disease. Neurobiol Aging. 1998; 19:161-163

32. Tamaoka A. [Characterization of amyloid β protein species in the plasma, cerebrospinal fluid and brains of patients with Alzheimer's disease] Nippon Ronen Igakkai Zasshi. 1998; 35:273-277

33. Kuo Y M, Kokjohn T A, Kalback W et al. Amyloid-beta peptides interact with plasma proteins and erythrocytes: implications for their quantitation in plasma. Biochem Biophys Res Commun. 2000; 268:750-756

34. Leonardi A, Gandolfo C, Caponnetto C et al. The integrity of the blood-brain barrier in Alzheimer's type and multi-infarct dementia evaluated by the study of albumin and IgG in serum and cerebrospinal fluid. J Neurol Sci. 1985; 67:253-261

35. Leblhuber F, Walli J, Tilz G P et al. [Systemic changes of the immune system in patients with Alzheimer's dementia]. Dtsch Med. Wochenschr. 1998; 123:787-791

36. Hawkins P N, Rossor M N, Gallimore J R et al. Concentration of serum amyloid P component in the CSF as a possible marker of cerebral amyloid deposits in Alzheimer's disease. Biochem Biophys Res Commun. 1994; 201:722-726

37. Myagkova M A, Qavrilova S I, Lermontova N N et al. Autoantibodies to beta-amyloid and neurotransmitters in patients with Alzheimer's disease and senile dementia of the Alzheimer type. Bull Exp Biol Med. 2001; 131:127-129

38. Walsh D M, Klyubin I, Fadeeva J V et al. Naturally secreted oligomers of amyloid beta protein potently inhibit hippocampal long-term potentiation in vivo. Nature. 2002; 416:535-539

39. Weksler M E, Goodhardt M. Do age-associated changes in 'physiologic' autoantibodies contribute to infection, atherosclerosis, and Alzheimer's disease? Exp Gerontol. 2002; 37:971-979

40. Lambert M P, Viola K L, Chromy B A et al. Vaccination with soluble Abeta oligomers generates toxicity-neutralizing antibodies. J. Neurochem. 2001; 79:595-605

41. Lambert M P, Barlow A K, Chromy B A et al. Diffusible, nonfibrillar ligands derived from Aβ1-42 are potent central nervous system neurotoxins. Proc Natl Acad Sci U S A. 1998; 95:6448-6453

42. Roher A E, Palmer K C, Yurewicz E C et al. Morphological and biochemical analyses of amyloid plaque core proteins purified from Alzheimer disease brain tissue. J Neurochem 1993; 61:1916-1926

43. Kuo Y M, Emmerling M R, Vigo-Pelfrey C et al. Water-soluble Aβ (N-40, N-42) oligomers in normal and Alzheimer disease brains. J Biol Chem 1996; 271:4077-4081

44. Atwood C S, Scarpa R C, Huang X et al. Characterization of copper interactions with alzheimer amyloid beta peptides: identification of an attomolar-affinity copper binding site on amyloid beta1-42. J. Neurochem. 2000; 75:1219-1233

45. Atwood C S, Huang X, Khatri A et al. Copper catalyzed oxidation of Alzheimer Abeta. Cell Mol Biol (Noisy-Le-Grand). 2000; 46:777-783

46. Atwood C S, Perry G, Zeng H et al. Copper Mediates Dityrosine Cross-Linking of Alzheimer's Amyloid-beta. Biochemistry. 2004; 43:560-568

47. Yoburn J C, Tian W, Brower J O et al. Dityrosine Cross-Linked Abeta Peptides: Fibrillar beta-Structure in Abeta(1-40) Is Conducive to Formation of Dityrosine Cross-Links but a Dityrosine Cross-Link in Abeta(8-14) Does Not Induce beta-Structure. Chem. Res Toxicol. 2003; 16:531-535

48. Lacroix-Desmazes S, Kaveri S V, Mouthon L et al. Self-reactive antibodies (natural autoantibodies) in healthy individuals. J Immunol Methods. 1998; 216:117-137

49. Oppezzo P, Dighiero G. [Autoantibodies, tolerance and autoimmunity]. Pathol Biol (Paris). 2003; 51:297-304

50. Xu S, Gaskin F. Increased incidence of anti-beta-amyloid autoantibodies secreted by Epstein-Barr virus transformed B cell lines from patients with Alzheimer's disease. Mech Ageing Dev. 1997; 94:213-222

51. Bush A I, Pettingell W H, Multhaup G et al. Rapid induction of Alzheimer Aβ amyloid formation by zinc. Science 1994; 265:1464-1467

52. Bush A I, Moir R D, Rosenkranz K M, Tanzi R E. Zinc and Alzheimer's disease-response. Science. 1995; 268:1921-1923

53. Rensink A A, de Waal R M, Kremer B, Verbeek M M. Pathogenesis of cerebral amyloid angiopathy. Brain Res Brain Res Rev. 2003; 43:207-223

Equivalents

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

We claim:

1. A method for diagnosing Alzheimer's disease in a subject comprising
    obtaining a blood or plasma sample from a subject,
    determining the presence of antibodies reactive with oxidized forms of amyloid β in the blood or plasma sample, wherein the lack of antibodies reactive with oxidized forms of amyloid β, or a reduced level of antibodies reactive with oxidized forms of amyloid β relative to a control indicates that the subject has Alzheimer's disease.

2. The method of claim 1, wherein the oxidized forms of amyloid β used to determine the presence of antibodies are cross-linked β-amyloid protein species (CLAPS).

3. The method of claim 2, wherein the CLAPS are 15-35 kDa.

4. The method of claim 2, wherein the CLAPS are formed by oxidation of amyloid β with horse radish peroxidase in the presence of hydrogen peroxide.

5. The method of claim 1, wherein the method used to determine the presence of antibodies reactive with oxidized forms of amyloid β is an ELISA assay.

6. The method of claim 1, wherein the ELISA assay is a sandwich ELISA assay.

7. The method of claim 1, wherein the control is blood or plasma from a non-demented individual.

* * * * *